United States Patent
Koike et al.

[11] Patent Number: 5,147,426
[45] Date of Patent: Sep. 15, 1992

[54] CENTRIFUGAL SEPARATOR FOR PREPARING AUTOMOTIVE EXHAUST GAS FOR POLLUTION TESTING WITH PRESSURE COMPENSATION

[75] Inventors: Hideki Koike; Junji Aoki, both of Miyanshigashi, Japan

[73] Assignee: Horiba, Ltd., Kyoto, Japan

[21] Appl. No.: 656,418

[22] Filed: Feb. 4, 1991

[30] Foreign Application Priority Data

Feb. 7, 1990 [JP] Japan .................. 2-27884

[51] Int. Cl.⁵ .............................. G01N 1/22
[52] U.S. Cl. .................. 55/270; 55/DIG. 30; 73/23.31; 137/171; 250/338.5; 494/56
[58] Field of Search ............ 73/23.2, 23.31, 25.01, 73/31.03, 31.04, 31.07, 863.21, 23.21, 28.01; 55/270, 210, DIG. 30; 137/171, 505.39, 505.41, 505.42; 210/109, 188, 360.1; 494/26, 56; 250/338.5

[56] References Cited

U.S. PATENT DOCUMENTS

| | | | |
|---|---|---|---|
| 3,085,742 | 4/1963 | Palmqvist | 494/56 |
| 3,451,421 | 6/1969 | Vicenzi et al. | 137/505.42 |
| 3,586,037 | 6/1971 | Zimmer | 137/505.42 |
| 3,593,023 | 7/1971 | Dodson et al. | 73/23.31 |
| 3,822,581 | 7/1974 | Hauck et al. | 73/23.31 |
| 4,160,373 | 7/1979 | Fastaia et al. | 73/23.31 |
| 4,555,931 | 12/1985 | Amimoto et al. | 73/23.31 |
| 4,747,297 | 5/1988 | Okayama et al. | 73/23.31 |
| 4,916,384 | 4/1990 | Ishida | 73/23.31 |

FOREIGN PATENT DOCUMENTS 1000515 4/1955 Fed. Rep. of Germany ..... 73/23.31

*Primary Examiner*—Robert A. Dawson
*Assistant Examiner*—Joseph Drodge
*Attorney, Agent, or Firm*—Price, Gess & Ubell

[57] ABSTRACT

As gas-liquid centrifugal separator includes a housing having a gas separating chamber that communicates with a source of a gas sample. A rotating plate can be positioned within the gas separating chamber for the centrifugal separation of liquids and/or solid particulates from the sample gas. The gas separating chamber is maintained at a pressure differential below that of the source of the gas sample. The discharge passageway communicates with the separating chamber to remove the separated liquid and solid particulates. A pressure regulator assembly is connected to the discharge passageway and a source of a pressurized gas in order to be responsive to variations in the pressure status of the discharge passageway and thereby vary the flow of the secondary pressurized gas to render the pressure level in the discharge passage constant to enable a constant effluence of the separated liquid and solid particulates.

5 Claims, 2 Drawing Sheets

CENTRIFUGAL SEPARATOR FOR PREPARING AUTOMOTIVE EXHAUST GAS FOR POLLUTION TESTING WITH PRESSURE COMPENSATION

BACKGROUND OF THE INVENTION

1. Field of the Invention

The present invention relates to a gas-liquid separator that can receive a sample gas into a gas-liquid separating chamber to enable a separation of gas from any liquids and/or solids by a centrifugal process and more particularly to an improved gas-liquid separator that can accommodate various pressure fluctuations in the sample gas.

2. Description of Related Art

Various types of gas-liquid separators have been utilized, for example, in analyzing the constituents existing in the exhaust gas of a motor vehicle to quantify the amount of air pollution. In this field, various kinds of gas-liquid separators for initially separating a sample gas having impurities from a liquid by a centrifugal processing have been utilized prior to providing the sample gas to an infrared analyzer for determining various air pollutants in the exhaust gas, such as $CO_2$, $NO_x$, HC and the like. An infrared analyzer that is used to analyze the air pollutants requires the gas sample to be appropriately prepared prior to an application of infrared rays in the measurement cycle. If, for example, moisture and solid impurities are introduced into the testing chamber of the infrared analyzer significant errors can occur. Thus, a gas-liquid separator having a high efficiency is particularly desired to prepare the gas specimen.

Referring to FIG. 3, a gas-liquid separator utilized in the prior art is disclosed. This gas-liquid separator 20 can be positioned between an engine exhaust pipe (not shown) and an infrared analyzer (not shown). A body portion 2 of the separator is provided with a gas-liquid separator chamber 3', a centrifugal separator assembly 4 and a drain pot 5. The gas-liquid separating chamber 3' is essentially a hollow chamber that communicates with a sample gas introducing pipe 6 that can be connected to the exhaust pipe of an engine at one end thereof. A second sample gas discharging pipe 7 can be connected to a vacuum section pump (not shown) for drawing off sample gas. The centrifugal separator 4 includes a motor 4a and an upper rotating plate 4b positioned in the hollow chamber. The motor 4a is arranged below the gas-liquid separating chamber 3' and an axis of a shaft of the motor 4a coincides with a longitudinal axis of the sample gas discharging pipe 7. A relatively small gap (g) or distance is provided between the upper surface of the rotating plate 4b adjacent the respective openings of the gas introducing pipe 6 and the sample gas discharging pipe 7 and the upper interior surface of the gas-liquid separating chamber 3' so that any sample exhaust flowing into the gas-liquid separating chamber 3' through the sample gas introducing pipe 6 will have any impurities of liquid and solid material discharged radially outward from the rotating plate 4b to ensure that any gas sample withdrawn by sample gas discharging pipe 7 will be free of such impurities.

A drain pot 5 is detachably mounted to the separator housing 2 and is capable of storing both liquid and solid impurities. This liquid storing vessel 5 is preferably made of glass or a transparent plastic and is screwed into a threaded connection formed adjacent an exhaust passage or port $3a'$ of the gas-liquid separating chamber 3'. Additionally, an end portion of a bypass pipe 8 is capable of communicating with a vacuum suction pump for use as a bypass (not shown) and can extend above the drain pot 5 so that the gas-liquid separating chamber 3' can be kept at a negative pressure to facilitate the introduction of any separated liquid into the drain pot 5. While not shown, the sample gas discharging pipe 7 can be provided with a pressure regulator so that a gas pressure of the gas sample supplied to an infrared analyzer can be regulated to a specific gas pressure level and the amount of sample gas introduced into the sample gas discharging pipe 7 is effectively controlled.

In operation, when an exhaust gas sample is introduced into the gas-liquid separator 20, both the vacuum suction pump for withdrawing a portion of the sampled gas and a vacuum suction pump for use in the bypass passageway 8 are started to maintain the gas-liquid separating chamber 3' at a negative pressure of approximately $-0.3$ $Kgf/cm^2$. During this time period, the centrifugal separator assembly 4 is operated so that when the exhaust gas discharged from the engine is introduced into the gas liquid separating chamber 3' by the conduit or pipe 6, it will contact the rotating plate 4b. Any liquids, such as water drops, and small particular solids, such as soot, that come into contact with the rotating plate 4b will be accelerated at a relatively high speed to be blown radially off of the rotating plate 4b in a centrifugal separation process. Such action will separate the exhaust gas with the sample gas being withdraw through the discharging pipe 7. The liquids and particulate materials that are separated are drawn by the negative pressure into the drain pot 5 for storage and subsequent discharge. As can be appreciated, the quantity of the liquids and solid particulates stored in the drain pot 5 will be progressively increased throughout the operation of an exhaust gas sampling procedure. An operator is required to monitor the drain pot 5 and to suitably remove it during a continuous analysis of the exhaust gas. This can cause maintenance problems and requires constant monitoring to ensure the proper operation of the gas-liquid separator 20.

In addition, the gas-liquid separating chamber 3' is designed to be kept at a negative pressure and there is always the possibility of a loss of such negative pressure by virtue of the bypass pipe 8. The suction pressure of a vacuum suction pump (not shown) connected to the bypass line 8 is not adapted to follow any internal pressure changes in the gas-liquid separating chamber 3' that can result with a fluctuation of the output of an engine. As a result, when the output of the engine is increased the internal pressure of the gas-liquid separating chamber 3' will also increase and the negative pressure condition that is desired can be lost and frequently it becomes difficult to draw or suck the centrifugally separated liquid and solid fraction toward the side of the drain pot 5. Also, the separated liquid and solid fraction can also be drawn directly into the bypass pipe 8 under certain circumstances and can clog up the bypass pipe 8 in an extreme case thereby disrupting the operation of the gas-liquid separator.

The prior art is still attempting to optimize the performance of gas-liquid separators.

SUMMARY OF THE INVENTION

The present invention addresses the problems mentioned above and provides a gas-liquid separator capable of an improved performance in separating a gas sample from an exhaust gas that can contain liquid and solid impurities even when the pressure of the exhaust gas introduced into a gas-liquid separating chamber, will fluctuate throughout the measurement cycle. The present invention attempts to minimize the maintenance requirements of a gas-liquid separator.

In the present invention a gas-liquid separator includes a gas separating chamber having a sample gas introduction port or pipe, a sample gas discharging port or pipe and a bypass port or pipe connected to the chamber. A centrifugal separator for separating liquid and solid particulates from a sample gas after receipt of exhaust gas is also provided. An exhaust passageway leading to a bypass pipe is further provided with a conduit or communication pipe specifically provided with a pressure regulator for regulating the internal pressure of the gas-liquid separating chamber to a predetermined pressure, despite any fluctuation of exhaust gas pressure from the gas introducing pipe. With this construction, exhaust gas provided to the gas-liquid separating chamber through the gas introducing pipe is not only subject to a centrifugal process for separating impurities in the form of liquid and solid particulates, but further the pressure maintained within the gas-liquid separating chamber can be easily controlled to predetermined conditions wherein not only a desired amount of sample gas can be withdrawn, but further any liquids and solids can be efficiently discharged without clogging the discharge bypass pipe.

The pressure regulator is connected to ambient air at atmospheric pressure, and is connected to the exhaust passageway in such a manner to vary the amount of ambient air that is introduced into the exhaust passageway in response to variation in pressure of the exhaust gas being introduced into the exhaust passageway resulting from variation of pressure of exhaust gas upstream being introduced into the gas-liquid separator. Thus, a negative pressure is maintained at a constant level to ensure a continual effluence of the separated waste products. The pressure regulator includes a spring-biased diaphragm that controls a valve member which can be set to a desired pressure level.

The features of the present invention which are believed to be novel are set forth in the appended claims. The present invention, both as to its organization and manner of operation, together with further objects and advantages, may best be understood by reference to the following description taken in conjunction with the accompanying drawings.

DESCRIPTION OF THE PREFERRED EMBODIMENTS

Figure 1:
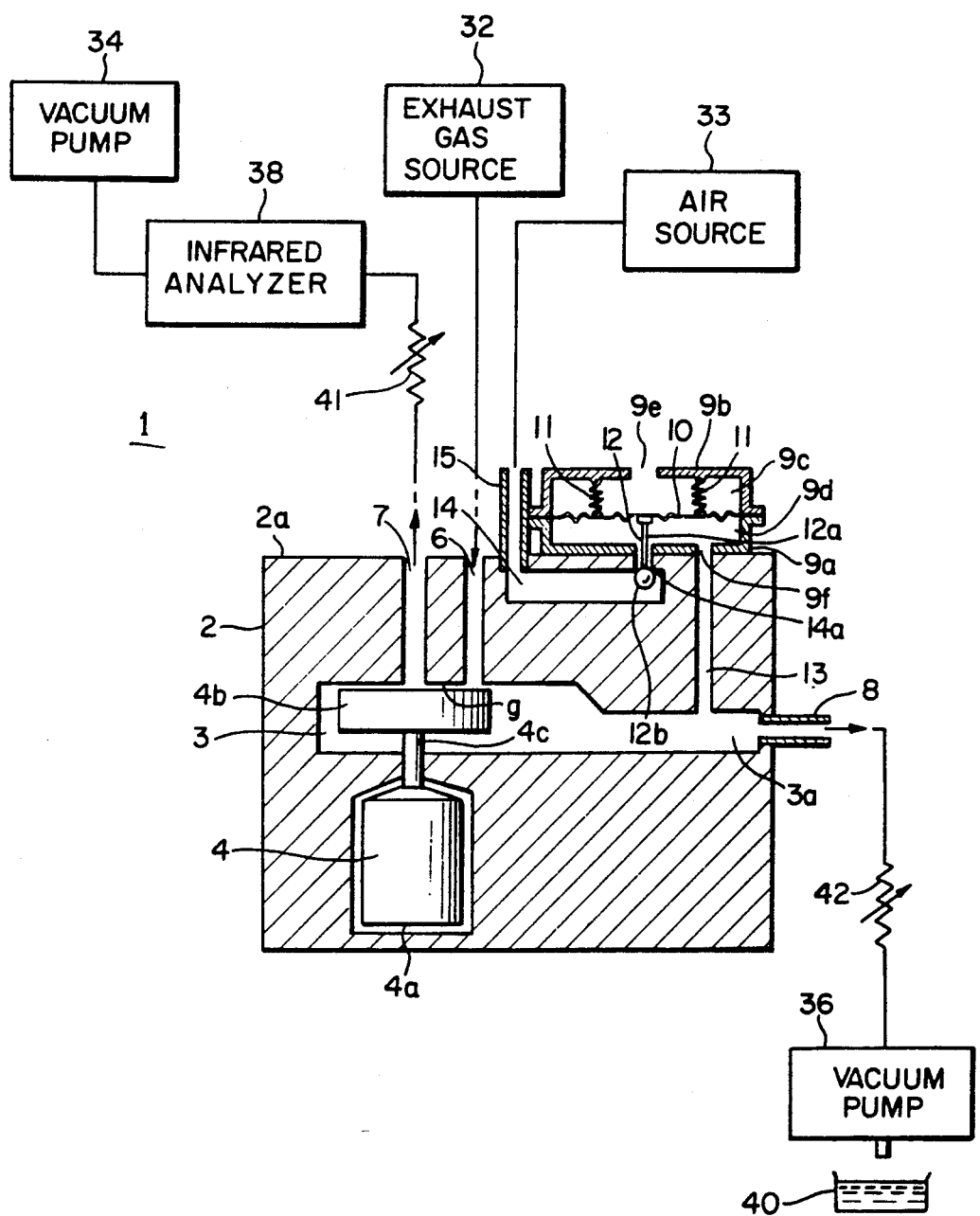
FIG. 1 is a schematic cross-sectional view disclosing a gas-liquid separator according to one preferred embodiment of the invention.

The following description is provided to enable any person skilled in the gas sampling art to make and use the invention and sets forth the best modes contemplated by the inventors of carrying out their invention. Various modifications, however, will remain readily apparent to those skilled in the art, since the generic principles of the present invention have been defined herein specifically to provide a relatively economically and easily manufactured gas-liquid separator.

In the drawings like reference parts will be described with the same reference number.

Referring to FIG. 1, a gas-liquid separator 1, according to a first preferred embodiment of the present invention, comprises a housing or body portion 2. The housing portion 2 includes an internal gas separating chamber 3 with a centrifugal separator assembly 4 mounted therein. A rotating plate 4b is offset from the upper internal surface of the gas-liquid separating chamber by distance g. The rotating plate 4b is supported on a shaft 4c and driven by a motor 4a. A sample gas discharging conduit or pipe 7 is aligned with the axis of the shaft 4c while a gas introducing pipe or conduit 6 is offset with this axis. Mounted on the body portion 2 is a pressure regulator assembly 9. Also communicating with the gas-liquid separating chamber 3 is a discharge port, passageway or conduit 3a that is connected to a bypass pipe 8 communicating with a vacuum suction pump 36.

The pressure regulator assembly 9 includes an upper chamber 9c and a lower chamber 9d that is separated by a flexible diaphragm 10 that is movably mounted within a case body 9a. The case body 9a is connected to a cover member 9b and is fixedly mounted on the upper surface 2a of the body portion 2. A pair of spring members 11 are positioned between an upper surface of the diaphragm 10 and mounting studs on the inner surface of the cover member 9b. These spring members 11 can bias the diaphragm 10 to an operative range of movement and can be adjustable for limiting an upper movement of the diaphragm 10. Mounted on the diaphragm 10, is a valve member 12 that includes a stem 12a which is formed into a spherical valving member 12b at one end. The cover member 9b is provided with an opening 9e communicating with the ambient air while the lower portion of the casing body 9a is provided with a pair of openings 9f and 9g with one opening 9f communicating directly through a passageway or communicating pipe 13 that is in fluid communication with the gas-liquid separating chamber 3. Communication pipe 13 opens directly into the discharge passageway 3a connected to the separating chamber 3. The other opening 9g communicates with a valve port opening 14a and a hollow passageway 14 formed in the upper portion of the housing portion 2. The valve member 10 extends through the respective openings 14a and 9a with the spherical valve member 12b being positioned within the hollow passageway 14.

An air supply pipe 15 is provided with an air filter (not shown) and is connected with the hollow passage 14 at one end thereof to supply the pressure regulator 9 with a pressure regulating gas, such as air from the air source 33.

The pressure regulator 9 is adapted to regulate the quantity of pressure regulating gas that can be supplementally supplied into the discharge passageway 3a depending upon a specific fluctuation of the exhaust gas coming from an exhaust gas source 32, such as an exhaust of an engine. The spring members 11 can be mounted for adjustment so that they can regulate the movement of the diaphragm 10 by balancing the gas pressure forces which in turn will regulate the position of the valve stem 12a and the respective opening clearance between spherical valve member 12b and the valve port opening 14a.

In operation, a pair of vacuum suction pumps 34 and 36 are actuated for withdrawing the sample gas through the discharge pipe 7 and for creating a negative pressure within the separating chamber 3 through communication with the discharge port 8. These vacuum suction pumps can be adjusted, for example, to keep the inside pressure of the gas-liquid separating chamber at a negative pressure of about $-0.3$ Kgf/cm$^2$. The pressure regulator 9 is further supplied with a source of pressure regulating gas 30, such as air through an air supply pipe 15 into the hollow passageway 14, as can be appreciated, the air source can be ambient air that is bled into the exhaust passageway by the negative pressure.

An appropriate selection of the pressure range created by the vacuum suction pumps, such as 34 or 36, and the valve opening of the pressure regulator 9 provides a datum level of negative pressure operation. Any normal anticipated variation of pressure fluctuations from the exhaust gas will be within a responsive range of operation of the pressure regulator 9 to open or close its valve opening to regulate the inflow of the auxiliary pressure regulating gas.

The centrifugal separator 4 is started so that the plate 4b rotates and a portion of the exhaust gas exhausted from the engine under analysis is then introduced into the gas-liquid separator chamber 3 by the sample gas introduction pipe 6. Any impurities contained within this exhaust gas, such as water drops and small particulate solids, such as soot, will come into contact with the rotary member 4b rotating at a relative high speed, and will be radially accelerated to provide a centrifugal separation of the exhaust gas. With the exhaust gas separated into solids and liquids and gases, a sample gas can then be withdrawn by the vacuum suction pump 34 connected to the gas discharging pipe 7 for introduction into an infrared analyzer 38. The separated liquids and solid particulates are removed from the gas-liquid separating chamber 3 as a result of the negative pressure and are discharged through the bypass pipe 8 into a sump 40. Additionally, the pressure regulator 9 will control the pressure regulating gas which can be supplementally added into the discharge passageway 3a through the passageway 13. The discharging material, such as the moisture and the soot is exhausted without sticking to the exhaust port 3a or the inside of the bypass pipe 8. In FIGS. 1, 41, 42 designate restrictors for flowrate regulation. During the gas sampling operation fluctuations in the output of the engine can produce respective fluctuations in the pressure of the sampled gas. For example, pressure at the sample inlet communicating with the gas introduction pipe 7 frequently can vary between a range of about $-0.1$ to 1 Kgf/cm$^2$ due to these fluctuations in the output of the engine. As a result, the internal pressure of the gas-liquid separating chamber 3 will also vary. The present invention utilizes the pressure regulator 9 to eliminate these fluctuations particularly in the vicinity of the entrance to the discharge passageway 3a so that a relative constant exit pressure can be maintained in passageway 3a. For example, if the desired regulated pressure is P, the atmospheric pressure being po, the area of the diaphragm is A, and the force of the springs being kx, the following force balance relationship is provided $$PA = poA - kx$$

If the output pressure of the engine is suddenly increased to increase the effective internal pressure of the gas-liquid separating chamber 3, the diaphragm 10 of the pressure regulator 9 will be moved upward and will likewise move the valve stem 12a and valve member 12b upward. As a result of this movement of the diaphragm 10 the opening between the spherical member 12b of the valve member 12 and the opening 14a of the valve seat will be reduced and the quantity of the pressure regulating gas introduced through the pressure regulator 9 from the passageway 14 will likewise be reduced. In essence, the increased pressure in the sampled gas will reduce the bled-in auxiliary gas pressure through the passageway 13. As a result, a relatively constant pressure will be maintained in the passageway 3a adjacent the exhaust pipe or conduit 8. Even though the internal pressure P of the gas-liquid separating chamber 3 can vary as a result of the fluctuation of the output of the engine under analysis, the total flow rate of the gas passing through the exhaust conduit 8 will remain constant and will not fluctuate.

Thus, the present invention not only permits the continued centrifugal separation of solids and liquids from the sampling gas, even if pressures vary from the introduced exhaust gas, but also ensures that the separated material can be continuously discharged without any interruption or any maintenance problems. As can be appreciated, even if the exhaust output of the engine reaches a maximum value, the internal pressure of the pressure regulating assembly 9 can, by an appropriate setting of the force of the springs, can regulate the applied suction force of the various vacuum pumps through control of the pressure of the regulating gas. If in operation the sampling gas pressure within the gas-liquid separating chamber 13 is suddenly reduced, valve member 12 can then be further opened to increase the quantity of the pressure regulating gas supplied from source 30 so that the pressure and flow rate for the conduit 13 and the exhaust pipe 8 can be maintained constant to prevent any interference in the discharge of the separated liquids and solid particulates.

Although the gas-liquid separator 1 of the present invention is described as being used with an engine and an infrared analyzer, in order to analyze an exhaust gas from a motor vehicle in the preferred embodiment, it can be appreciated that the present invention is not necessarily limited to this environment and can be used in other applications wherein a centrifugal process is necessary to a sampling gas and that sampling gas can be subject to varying pressure fluctuations.

Figure 2:
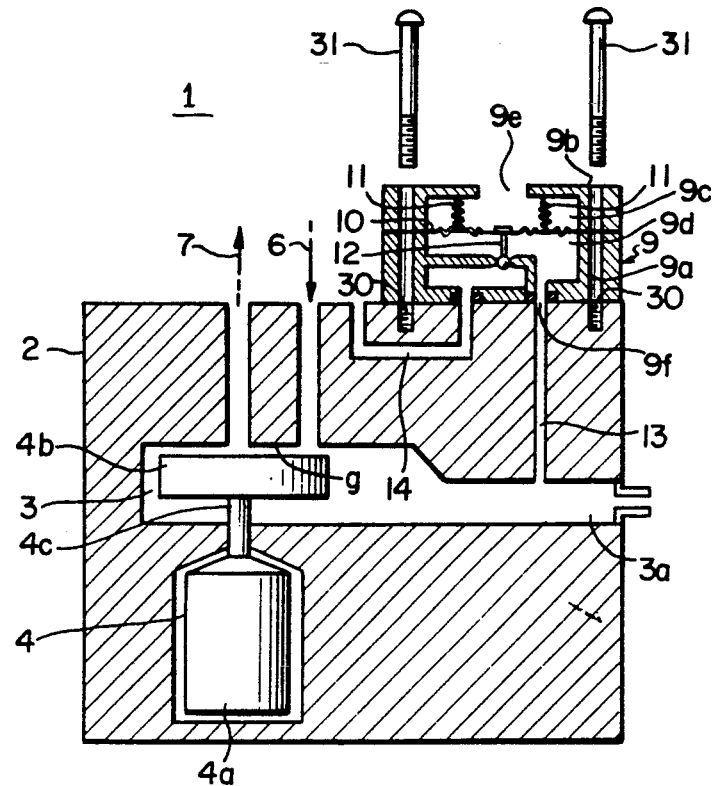
FIG. 2 is a schematic cross-sectional view showing another gas-liquid according to a second preferred embodiment of the present invention.
Figure 3:
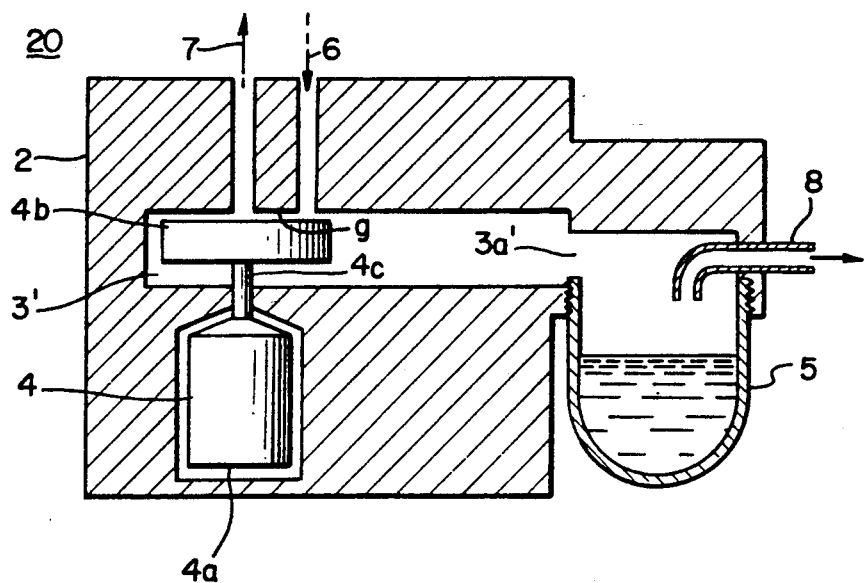
FIG. 3 is a schematic cross-sectional view showing a conventional gas-liquid separator.

In the embodiment disclosed in FIG. 2, the pressure regulator may be detachably mounted on the body portion 2 through the use of screw holes 30 and mounting screws 31.

As described above, an improved gas-liquid separator is provided with a pressure regulator capable of communication with a gas-liquid separating chamber so that the internal pressure of the gas-liquid separating chamber can accordingly be regulated even when fluctuating pressure occurs in the gas introducing pipe 6. As a result, the exhaust gas containing impurities, such as liquids and solids, can be continuously separated with the impurities being discharged throughout the sampling cycle. Problems in operation, that have occurred in the past, such as monitoring and removing drain pipes and physically dumping the liquids and solids are not necessary and maintenance for the discharge conduits are subsequently reduced.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A centrifugal separator system for treating exhaust gases comprising:

a housing having a separating chamber therein;

means for centrifugally introducing an exhaust gas into the introduced chamber;

means for separating the exhaust gas into gases and a fluid stream containing particulates of liquids and/or solids;

means for removing a predetermined portion of the separated gases substantially free of particulates;

means for removing the fluid stream from the housing by passing it into and through a discharge passageway, and means for providing a constant pressure, lower than pressure levels of the exhaust gas introduced into the chamber, in the discharge passageway, and means for regulating the pressure of the fluid stream in the discharge passageway at a relatively constant level despite any fluctuation in pressure levels of the exhaust gas introduced into the chamber including a pressure regulator assembly for compensating for any pressure fluctuation in the discharge passageway, the pressure regulator assembly including a valve connected to a source of gas at a pressure level higher than the provided constant pressure to the discharge passageway, the valve being responsive to any fluctuation in pressure levels in the fluid stream passing into the discharge passageway to control introducing of gas the amount from the gas source through the valve, whereby a constant effluence of separated liquids and/or solids is accomplished from the separator.

2. The separator system of claim 1 wherein the pressure regulator assembly includes a diaphragm connected to the pressure regulating valve.

3. In an infrared analyzer system for measuring a sample gas from an exhaust gas, the improvement comprising:

a housing having a separating chamber therein;

means for introducing an exhaust gas into the separating chamber;

means for centrifugally separating the introduced exhaust gas into gases and a fluid stream containing particulates of liquids and/or solids;

means for removing a predetermined portion of the separated, gases substantially free of particulates for introduction into an infrared analyzer system;

means for removing the fluid stream from the housing by passing it into and through a discharge passageway;

means for providing a pressure, lower than pressure levels of the exhaust gas introduced into the chamber, in the discharge passageway, and means for regulating the pressure of the fluid stream in the discharge passageway at a relatively constant level despite fluctuation in pressure levels of the exhaust gas including a pressure regulator assembly, the assembly including a valve responsive to any fluctuation in pressure levels of the fluid stream passing into the discharge passageway and a source of gas at a pressure level higher than the relatively constant pressure level in the discharge passageway connected to the pressure regulator assembly valve for compensating for any fluctuation in pressure levels whereby a constant effluence of separated liquids and/or solids is accomplished from the separator.

4. The infrared analyzer system of claim 3 wherein the pressure regulator assembly includes a diaphragm connected to the pressure regulating valve and the conduit so that the diaphragm is responsive to variations in pressure status of the discharge passageway.

5. The infrared analyzer system of claim 4 further including spring means for biasing the diaphragm.

* * * * *